United States Patent [19]
Burdick et al.

[11] Patent Number: 6,113,891
[45] Date of Patent: Sep. 5, 2000

[54] FLUIDIZED POLYMER SUSPENSIONS OF CATIONIC POLYSACCHARIDES IN EMOLLIENTS AND USE THEREOF IN PREPARING PERSONAL CARE COMPOSITIONS

[75] Inventors: Charles Lee Burdick, Landenberg, Pa.; Jacobus Johannes deBruin, Zwijnrdecht, Netherlands; Hans Hofman; Mohand Melbouci, both of Dordrecht, Netherlands

[73] Assignee: Hercules Incorporated, Wilmington, Del.

[21] Appl. No.: 09/200,350

[22] Filed: Nov. 20, 1998

Related U.S. Application Data

[60] Provisional application No. 60/066,199, Nov. 19, 1997.

[51] Int. Cl.[7] ............................. A61K 7/06; A61K 7/42; A61K 7/075
[52] U.S. Cl. ............... 424/70.13; 424/70.6; 424/70.14; 424/70.19; 424/70.22; 424/70.27; 424/70.31; 424/59; 424/68; 514/781; 524/394
[58] Field of Search ............................. 424/777, 781, 424/782; 514/781

[56] References Cited

U.S. PATENT DOCUMENTS

| | | | |
|---|---|---|---|
| 3,472,840 | 10/1969 | Stone et al. | 260/231 |
| 3,894,879 | 7/1975 | Colegrove | 106/189 |
| 3,894,880 | 7/1975 | Colegrove | 106/208 |
| 4,031,307 | 6/1977 | DeMartino et al. | 536/114 |
| 4,299,755 | 11/1981 | Keggenhoff et al. | 260/23 |
| 4,312,675 | 1/1982 | Pickens et al. | 106/171 |
| 4,325,861 | 4/1982 | Braun et al. | 523/205 |
| 4,374,216 | 2/1983 | Dammann | 524/35 |
| 4,453,979 | 6/1984 | DeMasi et al. | 106/188 |
| 4,566,977 | 1/1986 | Hatfield | 252/8.5 |
| 4,585,812 | 4/1986 | Field | 523/221 |
| 4,663,159 | 5/1987 | Brode, II | 514/844 |
| 4,799,962 | 1/1989 | Ahmed | 106/188 |
| 5,037,930 | 8/1991 | Shih | 527/301 |
| 5,080,717 | 1/1992 | Young | 106/197.1 |
| 5,096,490 | 3/1992 | Burdick et al. | 106/171 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,228,908 | 7/1993 | Burdick et al. | 106/194 |
| 5,228,909 | 7/1993 | Burdick et al. | 106/194 |
| 5,362,312 | 11/1994 | Skaggs et al. | 106/189 |
| 5,387,675 | 2/1995 | Yeh | 536/18.7 |
| 5,473,059 | 12/1995 | Yeh | 536/18.7 |
| 5,487,777 | 1/1996 | Lundan et al. | 106/188 |

FOREIGN PATENT DOCUMENTS

| | | |
|---|---|---|
| 2565109 | 12/1985 | France . |
| 54-135234 | 10/1979 | Japan . |
| 60-221493 | 11/1985 | Japan . |
| 10072340 | 3/1998 | Japan . |
| WO 97/46606 | 12/1997 | WIPO . |
| WO 97/493376 | 12/1997 | WIPO . |

OTHER PUBLICATIONS

W.L. Chiou et al Journal of Pharm. Sciences Sep. 1971 vol. 60, No. 9 pp. 1281–1302.

D.C. Steinberg, "Cosmetics and Toiletries Magazine", vol. 112, Jun., 1995, pp. 31–32.

*Primary Examiner*—Peter F. Kulkosky
*Attorney, Agent, or Firm*—Martin F. Sloan

[57] ABSTRACT

There are disclosed stable fluidized polymer suspensions containing cationic polysaccharide, stabilizing agent and emollient. The preferred cationic polysaccharides are cationic guar and cationic hydroxypropyl guar, and preferred emollients are hydrocarbons, silicone oils and esters. Processes for preparing personal care compositions utilizing the fluidized polymer suspensions are also disclosed. Using the fluidized polymer suspensions in the processes provides the advantages of more rapid dissolution and avoidance of lumps and gels when compared to using dry, powdered cationic polysaccharides.

56 Claims, No Drawings

FLUIDIZED POLYMER SUSPENSIONS OF CATIONIC POLYSACCHARIDES IN EMOLLIENTS AND USE THEREOF IN PREPARING PERSONAL CARE COMPOSITIONS

This application claims the benefit of U.S. Provisional Application No. 60/066,199 filed on Nov. 19, 1997; the disclosure which is incorporated by reference.

FIELD OF THE INVENTION

This invention relates to fluidized polymer suspensions of cationic polysaccharides and their use in preparing personal care compositions, in particular, hair and skin care compositions.

BACKGROUND OF THE INVENTION

Cationic polysaccharides have been used in many personal care applications, e.g. shampoos, shower gels, hair styling compositions, skin creams and lotions, where they provide theological properties to the compositions and desirable properties to the hair and skin.

Emollients are lipophilic materials that are utilized to smooth, soothe and lubricate the skin. They are quite often incorporated in cosmetic products to act as lubricants, reduce flaking and improve the appearance of the skin.

In most cases cationic polysaccharides used in personal care compositions are utilized as dry powders. However, handling of powders is often accompanied by dusting which can be a cause of health and safety problems. Moreover, in the case of cationic polysaccharides the dusting problem is particularly troublesome, because the cationic material tends to adhere strongly to anionic surfaces. Furthermore, particulate polysaccharides are known to lump excessively when added to water, resulting in low rates of solution, and so special care must be taken when adding these materials to water to avoid lumping and gel formation. Often, unacceptable gel levels remain in these solutions. For these reasons, there has been a desire to develop liquid cationic polysaccharide products that are readily dispersible in aqueous media, by dispersing them in liquids with which they are immiscible but which are useful in particular personal care applications.

Because emollients are widely used in personal care applications there is a particular advantage to be gained by having available fluidized polymer suspensions of cationic polysaccharides in emollients.

U.S. Pat. No. 4,312,675 discloses high concentration polymer slurries containing up to 65 wt. % xanthan gum in a hydrophobic solvent base treated with suspending agents, dispersants and thinning agents. Mineral oil, diesel oil, kerosene, alcohols ($C_6$–$C_2$), vegetable oil, ester-alcohols, polyol ethers and the like may be used as solvents.

U.S. Pat. No. 4,566,977 is directed to an improved non-aqueous slurry which comprises a water-soluble cellulose ether, a water-insoluble liquid hydrocarbon, a non-ionic surfactant having an HLB of from about 7 to about 14, and an organo modified clay. The water-soluble cellulose ethers are selected from anionic and nonionic cellulose ethers.

U.S. Pat. No. 5,096,490 discloses a fluid suspension of 35–55 parts of carboxymethyl cellulose or a similar polymer in 40 to 55 parts of fatty acid with 1 to 5 parts of clay and up to 20 parts of emulsifier. Guar and hydroxyproyl guar are included in the operable polymers disclosed.

None of these patents discloses fluidized polymer suspensions of cationic polysaccharides or their use in preparing personal care compositions.

The salvation and solubility properties of various water-soluble polysaccharides can vary widely. Therefore, information on fluidized polymer suspensions of anionic and nonionic polysaccharides is of little utility in predicting what systems will be suitable for preparing fluidized polymer suspensions of cationic polysaccharides.

SUMMARY OF THE INVENTION

In one embodiment of the invention a fluidized polymer suspension comprises: a) a cationic polysaccharide, b) a stabilizing agent, and c) an emollient that is a non-solvent for the cationic polysaccharide.

In another embodiment of the invention a process of preparing a personal care composition comprises: a) providing a fluidized polymer composition comprising I) cationic polysaccharide, ii) stabilizing agent, and iii) emollient that is a non-solvent for the cationic polysaccharide; and b) mixing the fluidized polymer suspension with one or more personal care active ingredients.

DETAILED DESCRIPTION OF THE INVENTION

It is characteristic of the fluidized polymer suspensions of this invention that they are stable as made. By the term "stable as made" it is meant that the suspension does not immediately separate into two or more distinct layers when standing. In some instances, where the suspension will be used within a short period of time, it is sufficient that the suspensions be moderately stable, i.e., at least sufficiently stable so that the cationic polysaccharide remains dispersed or may be readily redispersed after standing for a short period of time. However, dispersed cationic polysaccharides tend to agglomerate, upon settling, into gels or solids which cannot readily be redispersed after standing for more than a few days (or in some cases much shorter periods of time). Therefore it is often preferred that the suspensions be storage stable over much longer periods of time, because they will frequently be used in applications where they must be stored for periods of about one to six months. The fluidized polymer suspensions of this invention are stable as made, preferably stable for at least about one week, more preferably for at least about 8 weeks, and even more preferably for at least about 6 months.

Cationic polysaccharides for use in the invention include any naturally occurring cationic polysaccharide, as well as polysaccharides and polysaccharide derivatives that have been cationized by chemical means, e.g. quaternization with various quaternary amine compounds containing reactive chloride or epoxide sites. Example of such cationic polysaccharides include, but are not restricted to cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose. Preferred cationic polysaccharides for use in the invention are cationic guar and cationic hydroxypropyl guar.

Methods for preparation of the cationic polysaccharides are disclosed in U.S. Pat. Nos. 4,663,159, 5,037,930, 5,473,059, 5,387,675, 3,472,840 and 4,031,307, all of which are incorporated herein by reference in their entireties.

Emollients for use in the invention are non-solvents for the cationic polysaccharides (i.e., the cationic polysaccharides are soluble at a level of no more than about 5%) and are preferably liquids at room temperature. Emollients can be divided into the following classes: fatty alcohols, hydrocarbons, triglycerides, waxes, esters, silicone oils and lanolin containing products.

Examples of fatty alcohols are cetyl alcohol, octyldodecanol, stearyl alcohol, and oleyl alcohol.

Examples of hydrocarbons include mineral oil, petrolatum, paraffin, squalene, polybutene, polyisobutene, hydrogenated polyisobutene, cerisin and polyethylene.

There is a quite large group of triglycerides suitable for use in the invention. These include, but are not limited to, castor oil, caprylic/capric triglyceride, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadamia nut oil, olive oil, apricot kernel oil, hazelnut oil and borage oil.

Waxes useful as emollients include, but are not limited to, carnauba wax, beeswax, candelilla wax paraffin, Japan wax, microcrystalline wax, jojoba oil, cetyl esters wax, and synthetic jojoba oil.

The group of esters useful in the invention includes, but is not limited to, isopropyl myristate, isopropyl palmitate, octyl palmitate, isopropyl linoleate, $C_{12-15}$ alcohol benzoates, cetyl palmitate, myristyl myristate, myristyl lactate, cetyl acetate, propylene glycol dicaprylate/caprate, decyl oleate, stearyl heptanoate, diisostearyl malate, octyl hydroxystearate and isopropyl isostearate.

Lanolin containing products include lanolin, lanolin oil, isopropyl lanolate, acetylated lanolin alcohol, acetylated lanolin, hydroxylated lanolin, hydrogenated lanolin and lanolin wax.

Typical of silicone oils used for the invention are dimethicone (dimethyl polysiloxane) and cyclomethicone.

Preferred emollients for the invention are hydrocarbons, silicone oils and esters, particularly ones that are liquid at room temperature. More preferred emollients are mineral oil, polybutene and dimethicone.

In the fluidized polymer suspensions of the invention, preferably the cationic polysaccharide is from about 10 to about 65 wt. % and the emollient from about 35 to about 90 wt. % of the total weight of the fluidized polymer suspension. More preferably the cationic polysaccharide is from about 15 to about 60 wt. %, and the emollient from about 40 to about 85 wt. %. Most preferably the cationic polysaccharide is from about from about 20 to about 50 wt. %, and the emollient from about 50 to about 80 wt. % of the fluidized polymer suspension.

The other ingredient necessary in fluidized polymer suspensions of the invention is a stabilizing agent, preferably present at a level of from about 0.5 to about 5 wt. % of the total weight of the suspension. Preferred stabilizing agents are particulate organic or inorganic materials which can be dispersed or dissolved in the emollient medium. Preferred stabilizers include silica, mineral pigments, organic pigments, crosslinked polymers and copolymers of acrylic acid, cellulose ethers and mixtures thereof. More preferred are silica and mineral pigments. Examples of mineral pigments include, but are not limited to calcium carbonate, titanium dioxide, clay, organophilic clay, talc and gypsum. Preferred cellulose ethers for use as stabilizers are carboxymethyl cellulose and hydroxypropyl cellulose. The most preferred stabilizers are silica and organophilic clay. In mineral oil emollients, the most preferred stabilizer is organophilic clay.

The fluidized polymers suspensions may optionally contain water. If water is used, the amount should not be so great that the suspended cationic polysaccharide swells and forms a gel. Water is preferably used in an amount such that the ratio of cationic polysaccharide to water is not less than about 5:1.

Another optional ingredient in the fluidized polymer suspensions of this invention is surfactant. Surfactants may stabilize the dispersions and facilitate their blending with other ingredients used in preparing hair and skin care compositions.

Preferred surfactants for the invention are non-ionic surfactants, examples of which include, but are not restricted to, ethoxylated long chain fatty acids, sorbitan acid esters, polyoxyethylene alcohols, monoglycerides and diglycerides. Useful glycerides include glycerol monostearate, and mono- and diglycerides from glycerolysis of edible fats. Useful polyoxyethylene alcohols include polyoxyethylene lauryl ether, polyoxyethylene stearyl ether and polyoxyethylene oleyl ether. Particularly preferred surfactants comprise mixtures of sorbitan acid esters and polyoxyethylene sorbitan acid esters.

The amount of surfactant used in the fluidized polymer suspensions of the invention is preferably from about 0 to about 20% by weight based on the total weight of the fluidized polymer suspension. More preferably the amount is from 0 to about 10%, and most preferably from 0 to about 5%.

In order to prepare the fluidized polymer suspensions of the invention the emollient is added to a high shear mixing device, and then the appropriate stabilizing agent and surfactant, if used, are added. The mixture is stirred for a sufficient time to disperse the stabilizing agent, and the cationic polysaccharide is added. Further stirring is carried out until dispersion is complete. If water is utilized as a component of the fluidized polymer suspension, the water can be added with the cationic polysaccharide or the stabilizing agent. In most cases, the order of addition of the ingredients has no effect on the properties of the suspension. However, in systems utilizing mineral oil emollients and organophilic clay stabilizers, it is preferred that the surfactant or wetting agent be added after the organophilic clay has been activated.

The fluidized polymer suspensions of this invention find use in the formulation of personal care products, particularly hair and skin care compositions. Use of fluidized polymer suspensions of the cationic polysaccharides in place of dry powdered cationic polysaccharides has the advantages that the dusting, low rate of solution, lumping and gel formation of the powders is avoided.

Examples of personal care products of the invention include, but are not limited to shampoos, hair conditioners, combination shampoo-conditioners, sun screen products, shower gels, soaps, hair styling products, hair colorants, deodorants, antiperspirants, moisturizing lotions and the like.

The personal care products of the invention generally will comprise, in addition to the fluidized polymer suspension, some active component which provides benefit to the hair or skin. Such materials may include moisturizing agents, antiperspirants, anti-bacterials, sunscreen agents, cleaning agents, hair conditioning agents, hair styling agents, anti-dandruff agents, hair growth promoters, hair dyes and pigments, soaps and perfumes.

Typical moisturizing agents are animal oils such as lanolin and the like, fatty acid esters and fish oils; vegetable oils; mineral oils; petrolatum; and synthetic oils such as silicone oils.

A wide variety of sunscreen agents is suitable for use in the personal care compositions of the present invention. Examples include, p-aminobenzoic acid, its salts and its derivatives, anthranilates, salicylates, cinnamic acid derivatives, dihydroxy cinnamic acid derivatives, trihydroxy cinnamic acid derivatives, dibenzalacetone, dibenzalacetophenone, naphtholsulfonates, dihydroxynaphtholic acid and its salts, coumarin derivatives, diazoles, quinine salts, quinoline derivatives, hydroxy- and methoxy-substituted benzophenones, uric and vilouric acids, tannic acid and its derivatives, hydroquinone and benzophenones.

Typically, the active ingredient in deodorant-antiperspirant compositions is basic aluminum compound. Examples of such materials are aluminum chlorhydroxide, basic aluminum bromide, iodide or nitrate and basic aluminum hydroxy chloride-zirconyl hydroxy oxychloride.

Cleaning agents are typically anionic, cationic, non-ionic or amphoteric surfactants. Typical anionic surfactants are carboxylates, sulfonates, sulfates or phosphates, e.g. fatty acid soaps, salts of lauryl sulfate and salts of lauryl ether sulfate. Examples of cationic surfactants are aliphatic mono, di and polyamines derived from fatty and rosin acids, amine oxides, ethoxylated alkyl amines and imidazolines. Examples of non-ionic surfactants are polyoxyethylene surfactants, alkylphenol ethoxylates, carboxylic acid esters, e.g. mono and diglycerides, polyoxyethylene esters and fatty acid diethanolamine condensates. Amphoteric surfactants are those containing combinations of the anionic and cationic groups described above, particularly those containing both acid carboxyls and basic nitrogen groups. Typical amphoteric surfactants are imidazolines and betaines, e.g., lauric and myristic imidazolines and betaines, and amidopropylbetaines.

A wide variety of hair conditioning agents is useful in the compositions of this invention. Included are volatile hydrocarbons; silicones; cationic surfactants such as quaternary ammonium-containing cationic surfactants, e.g. di(hydrogenated tallow dimethyl ammonium chloride; hydrolyzed animal protein; and fatty alcohols.

Hair styling agents useful in the personal care compositions of the invention include the hair conditioning agents listed above as well as a wide variety of ionic and non-ionic polymers that are used to improve the manageability and hold of hair.

Typical soaps used as personal care active ingredients are salts of $C_8$–$C_{22}$ fatty acids.

Anti-dandruff agents, hair growth promoters and hair dyes and pigments may be any of those widely used in cosmetic formulations.

The personal care compositions of this invention contain active ingredient, and cationic polysaccharide as essential ingredients. In the case of the present invention, the cationic polysaccharide is introduced as a fluidized polymer suspension. Other ingredients, in addition to those already mentioned, may also be present. Examples of other ingredients include water; solvents; surfactants; colorants; antioxidants; vitamins; emulsifiers; opacifiers; pearlescent aids such as ethylene glycol distearate, or $TiO_2$ coated mica; pH modifiers such as citric acid, sodium citrate, succinic acid, phosphoric acid, sodium hydroxide and sodium carbonate; and preservatives such as benzyl alcohol, methyl paraben and propyl paraben.

The personal care compositions of this invention are readily prepared by use of conventional formulation and mixing techniques. Methods of making several personal care compositions using fluidized polymer suspensions containing cationic polysaccharides are described in the following examples, which are exemplary only and not intended to be limiting. All percentages, parts, etc., are by weight unless otherwise indicated.

EXAMPLE 1

This example describes preparation of a fluidized polymer suspension of cationic guar in polybutene.

Fifty (50) parts of polybutene (Indopol®N-14, from Amoco Chemical Co., Chicago, Ill.), was added to a mixing vessel, and then 2 parts of Tween®80 (polyoxyethylene sorbitan acid ester from Ruger Inc., Irvington, N.J.) was added and mixed. A quantity of 2 parts of Claytone®40 clay (from Southern Clay Products, Gonzales, Tex.) was added to the mixing vessel, and the resulting mixture was stirred to disperse the clay. After the clay was thoroughly mixed, 45 parts of N-Hance®GPX-3196 cationic guar (available from Hercules Incorporated, Wilmington, Del.) was added and stirred with high shear mixing to disperse. Finally, 1 part of water was added to the mixture and stirred to disperse.

The resulting product was fluid and pourable and was found to retain its homogeneity without appreciable settling for a period greater than 30 days. Upon addition to water the fluidized polymer suspension produced a rapid viscosity increase.

EXAMPLE 2

This example describes preparation of a fluidized polymer suspension of cationic hydroxypropyl guar in propylene glycol dicaprylate/dicaprate.

Two (2) parts of silica (Aerosil®200, available from Degussa AG, Hanau, Germany) was added to 68 parts of propylene glycol dicaprylate/dicaprate (Miglyol®840, available from Huels AG, Germany). The mixture was stirred using moderate shear, and after the silica was dispersed, 30 parts of cationic hydroxypropyl guar (N-Hance®Cationic HPGuar, available from Hercules Incorporated, Wilmington, Del.) was added. After stirring, a fluidized polymer suspension was obtained with a viscosity of 3,800 cps (LVT spindle #4, 30 rpm). The suspension was stable for at least one day.

EXAMPLE 3

This example describes preparation of a fluidized polymer suspension of cationic guar in mineral oil.

Tixogel®MP100 clay (from United Catalyst Inc., Louisville, Ken.), 3.4 parts, was added to 48.2 parts of white mineral oil (Marcol®52 CX from Exxon Company, Houston, Tex.) with stirring under high shear. Complete dispersion and swelling of the clay was achieved at temperatures in the range of 40–45° C. Then 0.37 parts of sorbitan ester trioleate (Montane®85 from Seppic, Paris, France) and 3.03 parts of ethoxylated sorbitan ester trioleate (Montanox®85 from Seppic) were added (other surfactant combinations can be used in such a way to achieve a hydrophilic/lipophilic balance (HLB) of about 10). Because the surfactants reduced the viscosity of the mixture, the shear rate was lowered before their addition. After the mixture was completely homogeneous, 45 parts of cationic guar (N-Hance®3000 from Hercules Incorporated, Wilmington, Del.) was added with vigorous agitation.

The resulting fluidized polymer suspension had a viscosity as made of 2,500 cps. After 24 hours the viscosity was 3,020 cps, after 1 week, 3,480 cps, after 1 month, 5,000 cps and after 4 months 5,000.

For measuring syneresis of the fluidized polymer suspension, glass flasks were filled to a 50 mm height with fluidized polymer suspension and then stored at room temperature and at 40° C. The height of the clear syneresis layer, if any was measured. The results are expressed as: height of syneresis (mm)/original height (50 mm). For example, "0.5/50" means 0.5 mm syneresis, 50 mm original height. The term "film" means a thin clear layer too small to be measured. The syneresis results are in Table 1.

TABLE 1

| Storage Time and Temp. | Syneresis |
| --- | --- |
| 24 hrs., room temp. | 0 |
| 24 hrs., 40° C. | 0 |
| 1 week, room temp. | 0 |
| 1 week, 40° C. | 0 |
| 1 month, room temp. | film |
| 1 month, 40° C. | 0.5/50 |
| 4 months, room temp. | 2/50 |
| 4 months, 40° C. | 6/50 |

To test the rate at which the cationic guar contained in the fluidized polymer suspension dissolved in water, fluidized polymer suspension was added to water in sufficient amount to provide a 2% solution of cationic guar in water. As a control, a similar solution was prepared using the same dry, powdered cationic guar used to prepare the fluidized polymer suspension. In both cases the pH was adjusted to below 7 and the mixtures were agitated.

Solution time for the dry powder was 30 minutes, and for the fluidized polymer suspension only 12 minutes.

EXAMPLE 4

This example describes preparation of a conditioning shampoo formulation using the fluidized polymer suspension of Example 3. For comparison, the same formulation was prepared using the same cationic guar, but in a dry powder form. The formulation is presented in Table 2.

TABLE 2

| INGREDIENT | PARTS PER HUNDRED |
| --- | --- |
| ammonium lauryl sulfate | 30 |
| cocamidopropyl betaine | 12 |
| propylene glycol | 5 |
| glycol stearate | 2 |
| hydrolyzed collagen | 2 |
| cocamide DEA | 1 |
| water | 47.7 |
| N-Hance ®3000 cationic guar | 0.3 |

The cationic guar, whether as the fluidized polymer suspension or a dry powder, was added as the last ingredient. When the fluidized polymer suspension was used, a sufficient amount was added to provide the level of cationic guar indicated. Hydration of the cationic guar began only after correction of the pH to about 5.5 by addition of citric acid.

Viscosities of the formulations were the same regardless of whether they were prepared from the fluidized polymer suspension or from powder. The fluidized polymer suspension dissolved quickly without formation of lumps. The appearance of the finished conditioning shampoo was pearlescent, white.

EXAMPLE 5

This example illustrates preparation of a cream rinse formulation utilizing the fluidized polymer suspension prepared in Example 3. For comparison, the same formulation was prepared using the same cationic guar, but in a dry powder form. The formulation is presented in Table 3.

TABLE 3

| | INGREDIENTS | WEIGHT % |
| --- | --- | --- |
| Part A | Water | As required to 100.00 |
| | N-Hance ®3000 cationic guar | 1.00 |
| | Glycerin | 1.00 |
| | Hydroxyethyl cellulose[1] | 0.40 |
| Part B | Stearalkonium chloride | 3.00 |
| | Cetyl alcohol | 2.00 |
| Part C | Preservative | 0.40 |
| | Fragrance | 0.30 |
| | Disodium EDTA | 0.10 |
| | Citric Acid | to pH 5.0 |

[1]Natrosol ®25OMR from Hercules Incorporated, Wilmington, DE

Part A was prepared by dispersing the cationic guar, either as a dry powder or fluidized polymer suspension, in water and reducing the pH of the water solution to 6–7. When the cationic guar was fully dissolved the hydroxyethyl cellulose was added, and the mixture was heated to 75–80° C. When all was fully dissolved, the glycerin was added. Part of the water was reserved to dissolve the disodium EDTA of Part C.

In a separate container Part B was mixed and heated to 75–80° C. It was then added with moderate stirring to Part A, and the resulting mixture was stirred until it was fully homogeneous and then cooled. When the temperature was below 30° C. the ingredients of Part C were added (the disodium EDTA as an aqueous solution), and the pH was adjusted to 5.0 with citric acid.

The viscosity of the cream rinse was essentially the same regardless of whether it was prepared using the cationic guar as a fluidized polymer suspension or the dry powder. In both cases the appearance of the formulations was excellent.

It is not intended that the examples presented here should be construed to limit the invention, but rather they are submitted to illustrate some specific embodiments of the invention. Various modifications and variations of the present invention can be made without departing from the scope of the appended claims.

What is claimed is:

1. A fluidized polymer suspension comprising:
    a) cationic polysaccharide at a level of from about 10 to about 65 wt. % of the total fluidized polymer suspension,
    b) stabilizing agent selected from the group consisting of silica, mineral pigments, organic pigments, crosslinked polymers and copolymers of acrylic acid, cellulose ethers and mixtures thereof at a level of from about 0.5 to about 5 wt. % of the fluidized polymer suspension, and
    c) emollient that is a non-solvent for the cationic polysaccharide, selected from the group consisting of fatty alcohols, hydrocarbons, triglycerides, waxes, esters, silicone oils and lanolins, said emollient being at a level of from about 35 to about 90 wt. % of the fluidized polymer suspension,
    wherein the fluidized polymer suspension is a liquid suspension of particulate cationic polysaccharide in the emollient, and is stable against agglomeration for at least one week.

2. The fluidized polymer suspension of claim 1 wherein the suspension is stable for at least about 8 weeks.

3. The fluidized polymer suspension of claim 1 wherein the suspension is stable for at least about 6 months.

4. The fluidized polymer suspension of claim 1 wherein the cationic polysaccharide is at least one member selected from the group consisting of cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose.

5. The fluidized polymer suspension of claim 1 wherein the cationic polysaccharide comprises cationic guar.

6. The fluidized polymer suspension of claim 1 wherein the cationic polysaccharide comprises cationic hydroxypropyl guar.

7. The fluidized polymer suspension of claim 1 wherein the emollient is at least one member selected from the group consisting of hydrocarbons, silicone oils and esters.

8. The fluidized polymer suspension of claim 1 wherein the emollient comprises a hydrocarbon selected from the group consisting of mineral oil, petrolatum, paraffin, squalene, polybutene, polyisobutene, hydrogenated polyisobutene, cerisin and polyethylene.

9. The fluidized polymer suspension of claim 1 wherein the emollient comprises dimethyl polysiloxane.

10. The fluidized polymer suspension of claim 1 wherein the emollient comprises a hydrocarbon selected from the group consisting of mineral oil and polybutene.

11. The fluidized polymer suspension of claim 1 wherein the emollient comprises polybutene.

12. The fluidized polymer suspension of claim 1 wherein the stabilizing agent comprises mineral pigment selected from the group consisting of calcium carbonate, titanium dioxide, clay, talc, organophilic clay, and gypsum.

13. The fluidized polymer suspension of claim 1 wherein the stabilizing agent comprises silica.

14. The fluidized polymer suspension of claim 1 wherein the stabilizing agent comprises clay.

15. The fluidized polymer suspension of claim 1 wherein the stabilizing agent comprises organophilic clay.

16. The fluidized polymer suspension of claim 1 further comprising a surfactant or mixture of surfactants, in an amount of from 0 to about 20% based upon the total weight of the fluidized polymer suspension.

17. The fluidized polymer suspension of claim 16 wherein the surfactant is selected from the group consisting of ethoxylated long chain fatty acids, sorbitan acid esters, monoglycerides or diglycerides and mixtures thereof.

18. The fluidized polymer suspension of claim 16 wherein the surfactant or mixture of surfactants has an HLB of about 10.

19. The fluidized polymer suspension of claim 1 further comprising water.

20. The fluidized polymer suspension of claim 1 wherein the cationic polysaccharide is from about 20 to about 50 wt. % of the total weight of the fluidized polymer suspension.

21. A process of preparing a personal care composition selected from the group consisting of shampoos, hair conditioners, combination shampoo-conditioners, sun screen products, shower gels, soaps, hair styling products, hair colorants, deodorants, antiperspirants and moisturizing lotions, comprising:
mixing the fluidized polymer suspension of claim 1 with one or more personal care active ingredients, wherein the fluidized polymer suspension modifies the rheological properties of the personal care composition.

22. The process of claim 21 wherein the fluidized polymer suspension is stable as made.

23. The process of claim 21 wherein the suspension is stable for at least about 1 week.

24. The process of claim 21 wherein the suspension is stable for at least about 8 weeks.

25. The process of claim 21 wherein the suspension is stable for at least about 6 months.

26. The process of claim 21 wherein the cationic polysaccharide comprises cationic guar.

27. The process of claim 21 wherein the cationic polysaccharide comprises cationic hydroxypropyl guar.

28. The process of claim 21 wherein the emollient is at least one member selected from the group consisting of hydrocarbons, silicone oils and esters.

29. The process of claim 21 wherein the emollient comprises a hydrocarbon selected from the group consisting of consisting of mineral oil, petrolatum, paraffin, squalene, polybutene, polyisobutene, hydrogenated polyisobutene, cerisin and polyethylene.

30. The process of claim 21 wherein the emollient comprises a hydrocarbon selected from the group consisting of mineral oil and polybutene.

31. The process of claim 21 wherein the emollient comprises polybutene.

32. The process of claim 21 wherein the stabilizing agent comprises mineral pigment selected from the group consisting of calcium carbonate, titanium dioxide, clay, organophilic clay, talc, and gypsum.

33. The process of claim 21 wherein the stabilizing agent comprises silica.

34. The process of claim 21 wherein the stabilizing agent comprises clay.

35. The process of claim 21 wherein the stabilizing agent comprises organophilic clay.

36. The process of claim 21 wherein the fluidized polymer suspension further comprises a surfactant or mixture of surfactants, in an amount of from 0 to about 20% based upon the total weight of the fluidized polymer suspension.

37. The process of claim 36 wherein the surfactant is selected from the group consisting of ethoxylated long chain fatty acids, sorbitan acid esters, monoglycerides or diglycerides and mixtures thereof.

38. The process of claim 36 wherein the surfactant is a mixture of sorbitan acid ester and polyoxyethylene sorbitan acid ester.

39. The fluidized polymer suspension of claim 36 wherein the surfactant or mixture of surfactants has an HLB of about 10.

40. The process of claim 21 wherein the fluidized polymer suspension further comprises water.

41. The process of claim 21 wherein the cationic polysaccharide comprises cationic guar, the emollient that is a non-solvent for the cationic polysaccharide comprises polybutene, and the stabilizing agent comprises clay.

42. The process of claim 21 wherein the personal care composition is a shampoo and the personal care active ingredient comprises surface active cleaning agent.

43. The process of claim 21 wherein the personal care composition is a hair conditioner and the personal care active ingredient is selected from the group consisting of cationic surfactant, hydrolyzed animal protein, fatty alcohols, silicones, volatile liquid hydrocarbons, and mixtures thereof.

44. The process of claim 21 wherein the personal care composition is a shampoo-conditioner and the personal care active ingredient comprises surface active cleaning agent and hair conditioning ingredient selected from the group consisting of cationic surfactant, hydrolyzed animal protein, fatty alcohols, silicones, volatile liquid hydrocarbons, and mixtures thereof.

45. The process of claim 21 wherein the personal care composition is a shower gel and the personal care active ingredient comprises surface active cleaning agent.

46. The process of claim 21 wherein the personal care composition is a hair styling gel and the personal care active ingredient comprises cationic or anionic hair styling polymer.

47. The process of claim 21 wherein the personal care composition is a hair colorant and the personal care active ingredient comprises a hair coloring agent.

48. The process of claim 21 wherein the personal care composition is a deodorant-antiperspirant composition and the personal care active ingredient comprises a basic aluminum compound.

49. The fluidized polymer suspension of claim 16 wherein the surfactant is a mixture of sorbitan acid ester and polyoxyethylene sorbitan acid ester.

50. The fluidized polymer suspension of claim 1 wherein the cationic polysaccharide is from about 15 to about 60 wt. % of the total weight of the fluidized polymer suspension.

51. The fluidized polymer suspension of claim 1 wherein the cationic polysaccharide comprises cationic guar, the emollient that is a non-solvent for the cationic polysaccharide comprises polybutene, and the stabilizing agent comprises clay.

52. The fluidized polymer suspension of claim 1 wherein the lanolins are selected from the group consisting of lanolin, lanolin oil, isopropyl lanolate, acetylated lanolin alcohol, acetylated lanolin, hydroxylated lanolin, hydrogenated lanolin and lanolin wax.

53. The process of claim 21 wherein the cationic polysaccharide is at least one member selected from the group consisting of cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose.

54. The process of claim 21 wherein the emollient comprises dimethyl polysiloxane.

55. The process of claim 21 wherein the lanolins are selected from the group consisting of lanolin, lanolin oil, isopropyl lanolate, acetylated lanolin alcohol, acetylated lanolin, hydroxylated lanolin, hydrogenated lanolin and lanolin wax.

56. The process of claim 21 wherein the personal care composition is a sun care product and the personal care active ingredient comprises a sunscreen agent.

* * * * *